(12) United States Patent
Guzman et al.

(10) Patent No.: US 6,506,206 B1
(45) Date of Patent: Jan. 14, 2003

(54) GEL TOURNIQUET CUFF

(75) Inventors: Jose F. Guzman, Warsaw, IN (US); Christian H. Clupper, Columbia City, IN (US); Conrad L. Klotz, Nappanee, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/482,737

(22) Filed: Jan. 13, 2000

Related U.S. Application Data

(63) Continuation-in-part of application No. 09/467,521, filed on Dec. 21, 1999, now abandoned.
(60) Provisional application No. 60/114,726, filed on Dec. 31, 1998.

(51) Int. Cl.[7] .............................................. A61B 17/137
(52) U.S. Cl. ..................................................... 606/203
(58) Field of Search ................................ 606/202, 203, 606/204; 128/78, 68, 327, 201

(56) References Cited

U.S. PATENT DOCUMENTS

| 2,841,149 A | | 7/1958 | Marsden | |
| 3,513,831 A | | 5/1970 | Hirsch | |
| 3,730,186 A | * | 5/1973 | Edmunds, Jr. et al. | 128/325 |
| 4,228,792 A | | 10/1980 | Rhys-Davies | |
| 4,255,202 A | | 3/1981 | Swan | |
| 4,637,394 A | | 1/1987 | Racz et al. | |
| 4,979,953 A | | 12/1990 | Spence | |
| 4,993,409 A | | 2/1991 | Grim | |
| 5,201,758 A | | 4/1993 | Glover | |
| 5,383,893 A | * | 1/1995 | Daneshver | 606/201 |
| 5,421,874 A | | 6/1995 | Pearce | |
| 5,456,072 A | | 10/1995 | Stern | |
| 5,549,743 A | | 8/1996 | Pearce | |
| 5,626,657 A | | 5/1997 | Pearce | |
| 5,636,395 A | | 6/1997 | Serda | |
| 5,660,182 A | * | 8/1997 | Kurishaki et al. | 606/202 |
| 5,733,304 A | | 3/1998 | Spence | |
| 5,776,088 A | | 7/1998 | Sereboff | |
| 6,020,055 A | | 2/2000 | Pearce | |

* cited by examiner

Primary Examiner—Eduardo C. Robert
(74) Attorney, Agent, or Firm—Barnes & Thornburg

(57) ABSTRACT

A tourniquet cuff (10) includes a first layer (20), a second layer (40), and a third layer (60). The first layer (20) has an inner side (22) impermeable to air and the second layer (40) has a first side (44) impermeable to air. The inner side (22) of the first layer (20) and the first side (44) of the second layer (40) cooperate to define a first cavity (96) formed to receive a gel-like material (15) therein. Further, the third layer (60) has an inner side (64) which cooperates with a second side (42) of the second layer (40) to define a second cavity (94) formed to receive pressurized air. The tourniquet cuff (10) adjustably secures about a patient's limb such that the gel-like material (15) is positioned between the patient's limb and the second cavity (94) to uniformly and comfortably distribute pressure around the patient's limb.

15 Claims, 4 Drawing Sheets

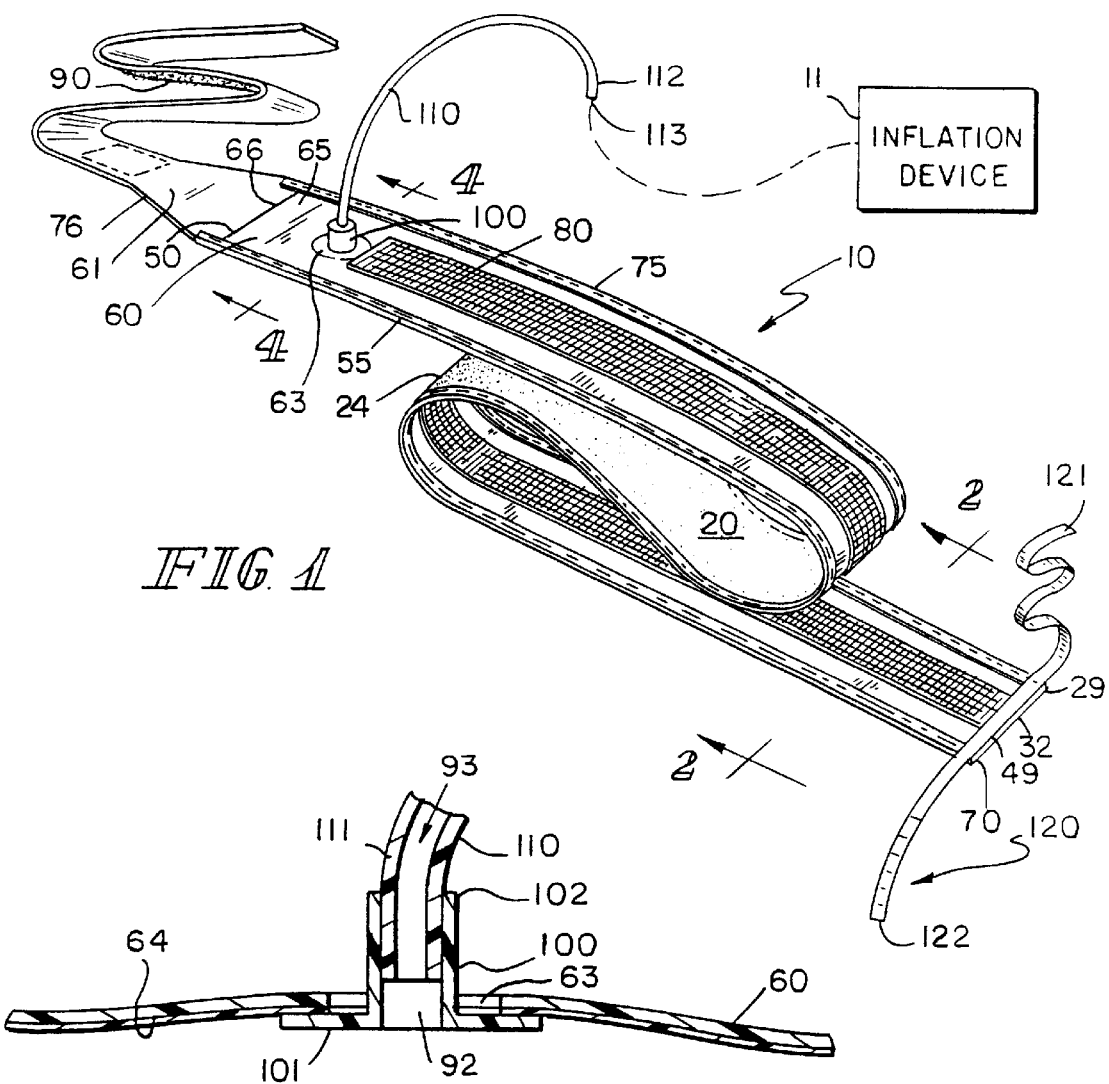
FIG. 1
FIG. 4
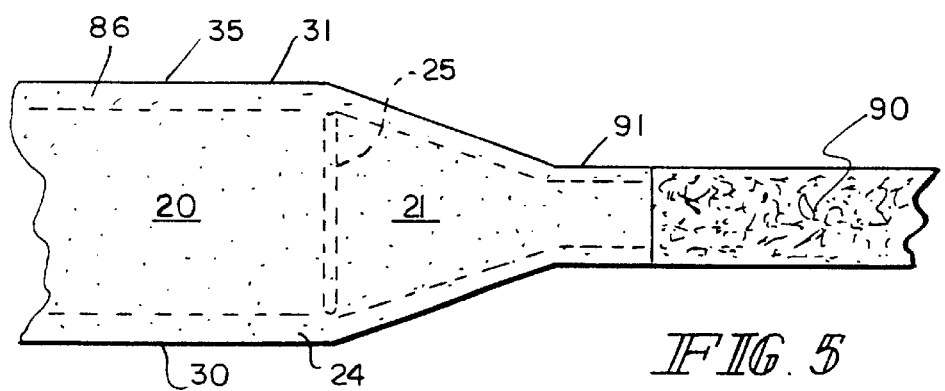
FIG. 5

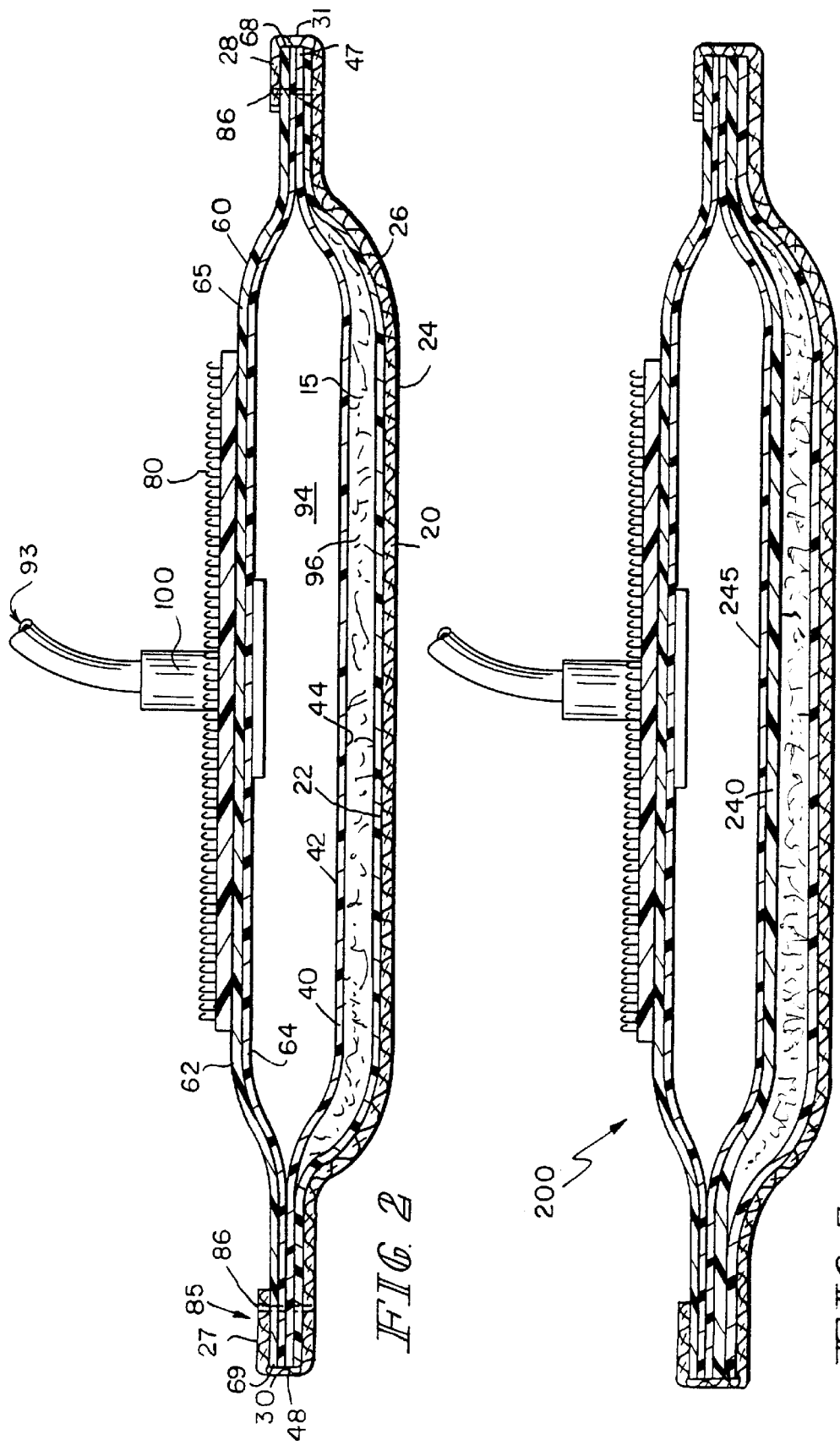

GEL TOURNIQUET CUFF

GEL TOURNIQUET CUFF

This application is a continuation-in-part of U.S. application Ser. No. 09/467,521, filed Dec. 21, 1999, now abandonded, which claims priority under U.S.C. §119(e) to U.S. Provisional Application No. 60/114,726, filed Dec. 31, 1998, which is expressly incorporated by reference herein.

FIELD OF THE INVENTION

The present invention relates to a tourniquet cuff and particularly to a tourniquet cuff for providing uniform pressure distribution and patient comfort.

BACKGROUND AND SUMMARY OF THE INVENTION

Tourniquet cuffs are used to reduce the flow of blood to a location on the human body where surgery is taking place. Typically, tourniquet cuffs employ a cotton layer which wraps around the patient's arm or leg at a point proximal to the heart from where surgery is being performed. During use, the cotton layer is positioned adjacent to the patient's limb. An expandable air bladder surrounds the cotton layer to allow various pressures to be applied to the cotton layer, and thus, to the patient's limb. By providing pressure around a patient's limb, the tourniquet cuff reduces the flow of blood to that portion of the limb distal to the tourniquet cuff and toward the limb's extremity. The cotton layer is employed so that the tourniquet cuff may be placed comfortably on the patient's limb.

According to one embodiment of the present invention, a tourniquet cuff is provided to distribute pressure more evenly and for better patient comfort than is provided by traditional tourniquet cuffs. The tourniquet cuff of the present invention includes a gel layer within the tourniquet cuff. Adjacent to the gel layer is an air bladder which is inflated to provide pressure around a patient's limb. As an alternative to an air bladder, other devices, such as a simple strap, may be used to provide pressure around the patient's limb. During use, the air bladder is inflated around the patient's limb with the gel layer positioned between the patient's limb and the air bladder. The gel layer conforms to the particular patient's limb for added comfort and better pressure distribution than may be provided by traditional tourniquet cuffs. Another object of the present invention is to provide a funnel-shaped (tapered) section at one end of the tourniquet to allow the tourniquet to resist folding and buckling and to allow the tourniquet to conform more comfortably to the patient's limb.

In a preferred embodiment, a length of polyester nap material and two lengths of nylon material are positioned in layers and sealed together at their perimeters to create two bladders and define two air-tight chambers—a first chamber between the polyester nap layer and the middle nylon layer and a second chamber between the middle nylon layer and the outer nylon layer. A gel-like material is positioned within the first chamber and the second chamber can be inflated to provide increased pressure to a patient's limb when the tourniquet is around the patient's limb.

The polyester nap material and the top nylon layer each have a tapered portion, one coupled to the other, each having a wide end and a narrow end, the wide end of the polyester nap material and the wide end of the top nylon layer being coupled to one end of the two bladders. A VELCRO loop-portion strap is coupled to the narrow end of the polyester nap material and to the narrow end of the top nylon layer. A VELCRO hook-portion strap is attached to the top surface of the second chamber for securing the tourniquet cuff about the patient's limb.

In yet another embodiment, a length of polyester nap material and a first length of nylon material are positioned in layers and sealed together at their perimeters to create a first chamber. A gel-like material is positioned within the first chamber. A second length and a third length of nylon material of substantially the same dimensions as the first chamber are positioned in layers and sealed together at their perimeters and also lengthwise down their approximate middles to create second and third parallel airtight chambers. The second and the third chambers can be inflated independently of each other to provide increased pressure to a patient's limb when the tourniquet is around the patient's limb.

In yet a further embodiment, an elongated chamber is wrapped and fastened about a patient's limb and inflated to apply pressure to the limb and reduce or eliminate blood flow. An additional chamber is secured to the inflatable chamber to extend therealong and to be disposed between the inflatable chamber and the surface of the patient's limb. A gel-like substance is disposed within the additional chamber to distribute pressure uniformly and comfortably on the patient's limb.

Additional features and advantages of the invention will become apparent to those skilled in the art upon consideration of the following detailed description exemplifying the best mode of carrying out the invention as presently perceived.

BRIEF DESCRIPTION OF THE DRAWINGS

FIG. 1 is a perspective view of the gel tourniquet cuff in accordance with the present invention;

FIG. 2 is a sectional view of the tourniquet of FIG. 1 taken along line 2—2;

FIG. 3 is a sectional view similar to that shown in FIG. 2 illustrating an additional embodiment of the present invention;

FIG. 4 is a sectional view of a bladder port of the tourniquet of FIG. 1 taken along the line 4—4;

FIG. 5 is a plan view of one end of the tourniquet of FIG. 1, showing a VELCRO loop portion coupled to a polyester nap funnel-shaped end of the tourniquet;

DETAILED DESCRIPTION

Figure 6:
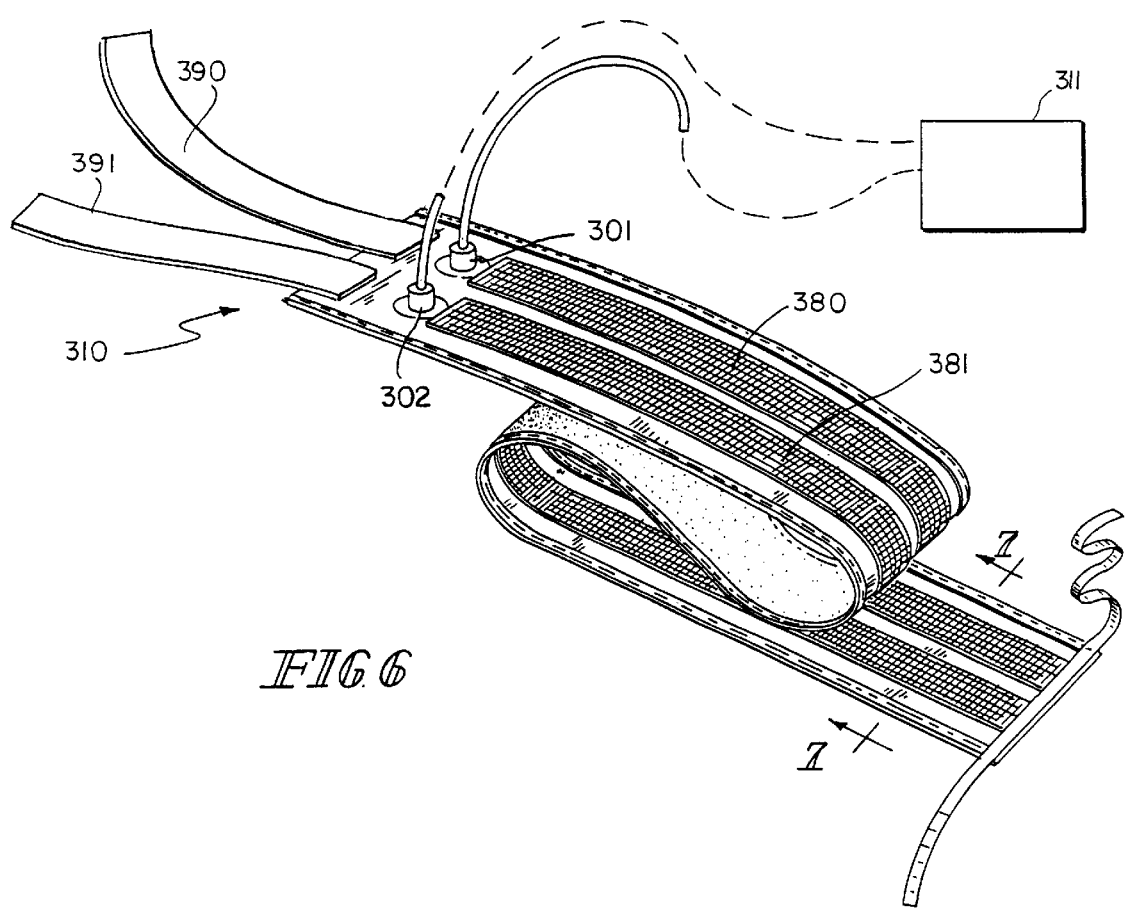
FIG. 6 is a perspective view showing another embodiment of the gel tourniquet cuff in accordance with the present invention.

Tourniquet cuff 10, shown in FIG. 1, includes a polyester nap layer 20, an outer nylon layer 60, a VELCRO hook-portion 80, a VELCRO loop-portion 90, a polyurethane bladder port 100 (best seen in FIG. 4), a PVC tube 110 (best seen in FIG. 4), and a tie 120 having first and second tie ends 121, 122. Polyester nap layer 20 and outer nylon layer 60 are generally rectangular in shape except for a polyester nap funnel-shaped end 21 (FIG. 5) and an outer nylon funnel-shaped end 61, including a funnel perimeter 76.

Referring now to FIGS. 1, 2, and 5, polyester nap layer 20 includes a first nap side 22, a second nap side 24, and first, second, and third nap fold portions 27, 28, and 29 folded along first, second, and third nap folds 30, 31, and 32. Further, polyester nap layer 20 includes a nap-funnel boundary 25 and a nap perimeter portion 35 located adjacent first, second, and third nap folds 30, 31, 32, a nap funnel boundary 25, and a funnel-shaped end 21. For patient comfort, polyester nap layer 20 may have a felt-like texture which remains exposed on second nap side 24. However, first nap side 22 may be coated with a thin (illustratively 4 mil) layer of polyurethane 26 to produce a surface impervious to the gel-like material 15 (best seen in FIG. 2). It is understood that within the scope of this disclosure, materials other than polyurethane may be used to form such an impervious surface. Also, other materials, including soft cotton and other comfortable materials, may be used for polyester nap layer 20.

As best seen in FIG. 2, adjacent to polyester nap layer 20 is a middle nylon layer 40, including a first middle nylon side 42, a second middle nylon side 44, a first middle nylon edge 47, and a second middle nylon edge 48. As best seen in FIG. 1, middle nylon layer 40 also includes a third middle nylon edge 49, a fourth middle nylon edge 50, and a middle nylon perimeter portion 55 located adjacent to the first, second, third, and fourth middle nylon edges 47, 48, 49 and 50. First middle nylon side 42 and second middle nylon side 44 are preferably coated with thin (illustratively 4 mil) layers of polyurethane to produce air-impenetrable surfaces. Again, it is understood that materials other than polyurethane may be used to form such air-impenetrable surfaces and that materials other than polyurethane-coated nylon may be used for the middle nylon layer. Middle nylon layer 40 is the same, generally rectangular, shape as polyester nap layer 20 and outer nylon layer 60, except that, as shown, middle nylon layer 40 does not include a funnel-shaped end. However, to provide additional structural support, middle nylon layer 40 may be provided with a funnel-shaped end similar to funnel-shaped end 21. Further, in the illustrative embodiment, middle nylon layer 40 is slightly smaller than polyester nap layer 20, so that when second middle nylon side 44 is positioned adjacent first nap side 22 and outer nylon layer 60 is positioned adjacent to middle nylon layer 40, first, second and third nap fold portions 27, 28, 29 extend beyond first, second, and third middle nylon edges 47, 48, 49 and polyester nap funnel-shaped end 21 extends beyond fourth middle nylon edge 50. As discussed below, this arrangement aids in the formation of tourniquet cuff 10 of the preferred embodiment.

Preferably, middle nylon layer 40 is a fairly stiff material, having a denier greater than 200. In a preferred embodiment, middle nylon layer 40 is approximately a 420 denier nylon material. Such a material provides sufficient stiffness to prevent the tourniquet cuff 10 from rolling down the patient's limb, while providing enough flexibility to allow for satisfactory pressure distribution characteristics.

As shown in FIGS. 1 and 2, adjacent to middle nylon layer 40 is outer nylon layer 60, which includes a main outer nylon body 65, a first outer nylon side 62, a second outer nylon side 64, a first outer nylon edge 68, a second outer nylon edge 69, and a third outer nylon edge 70. Further, outer nylon layer 60 includes an outer nylon funnel boundary 66 between main outer body 65 and outer nylon funnel-shaped end 61, and an outer perimeter portion 75 located adjacent first, second, and third outer nylon edges 68, 69, and 70 and outer nylon funnel boundary 66 (best seen in FIG. 1). As with sides 22, 42, and 44, second outer nylon side 64 is preferably coated with a thin (illustratively 4 mil) layer of polyurethane to produce an air-impenetrable surface, but it is understood that materials other than polyurethane may be used to form such an air-impenetrable surface. As illustrated, outer nylon layer 60 is the same, generally rectangular, shape as polyester nap layer 20, including outer nylon funnel-shaped end 61, which is the same general shape and size as polyester nap funnel-shaped end 21. However, as with middle nylon layer 40, outer nylon layer 60 is slightly narrower and shorter than polyester nap layer 20, so that first, second, and third nap fold portions 27, 28, 29 extend beyond first, second, and third outer nylon edges 68, 69, and 70. Lastly, an aperture 63 is formed in outer nylon layer 60 (best seen in FIG. 4).

Referring to FIGS. 1 and 4, polyurethane bladder port 100 includes a bladder flange 101 and a bladder nozzle 102. As illustrated, bladder nozzle 102 is inserted through aperture 63 in outer nylon layer 60 so that bladder flange 101 abuts second outer nylon side 64. Bladder flange 101 is affixed to second outer nylon side 64, coupling bladder port 100 to outer nylon layer 60. As best seen in FIGS. 1, 2, and 4, with bladder port 100 coupled to outer nylon layer 60, second outer nylon side 64 is positioned adjacent first middle nylon side 42 so that first, second, and third middle nylon edges 47, 48, 49 line up with first, second, and third outer nylon edges 68, 69, 70, and outer perimeter portion 75 is positioned adjacent middle nylon perimeter portion 55. First nap side 22 is then positioned adjacent second middle nylon side 44 so that first, second, and third nap folds 30, 31, 32 line up with first, second, and third middle nylon edges 47, 48, 49, and first, second, and third outer nylon edges 68, 69, 70. Thus, nap perimeter portion 35 is positioned adjacent middle nylon perimeter portion 55. Therefore, in the illustrated embodiment, middle nylon layer 40 is sandwiched between polyester nap layer 20 and outer nylon layer 60. With the three layers 20, 40, and 60 in position, heat and pressure is applied to nap perimeter portion 35, middle nylon perimeter portion 55, and outer nylon perimeter portion 75 simultaneously, creating a heat seal 85 binding the three layers 20, 40, and 60 together. However, it is understood that other methods of binding the layers together are possible within the scope of this invention. Further, heat seal 85 is air-impenetrable so that an air chamber 94 is created between first middle nylon side 42 and second outer nylon side 64. Bladder port 100 provides an opening 92 (best seen in FIG. 4) defining a passageway 93 into air chamber 94. However, other than opening 92, air chamber 94 is air-tight. Heat seal 85 also creates a gel chamber 96 between first nap side 22 and second middle nylon side 44. Prior to binding layers 20, 40, and 60 together, a gel-like material 15 is positioned within gel chamber 96. Therefore, when layers 20, 40, and 60 are bound together, gel-like material 15 is sealed within gel chamber 96.

In an alternative embodiment of the tourniquet cuff 200 (FIG. 3), the middle nylon layer 40 of FIG. 2 is replaced by multiple layers 240 and 245, one cooperating with polyester nap layer 20 to create gel chamber 96 and another cooperating with outer nylon layer 60 to create air chamber 94. Also, in another alternative embodiment, gel-like material 15 is pre-sealed within its own flexible packaging (not shown), and the entire gel-like material package is shaped and positioned within gel chamber 96. In this embodiment, gel chamber 96 need not be sealed, thus allowing easy removal and replacement of the gel-like material package.

Figure 7:
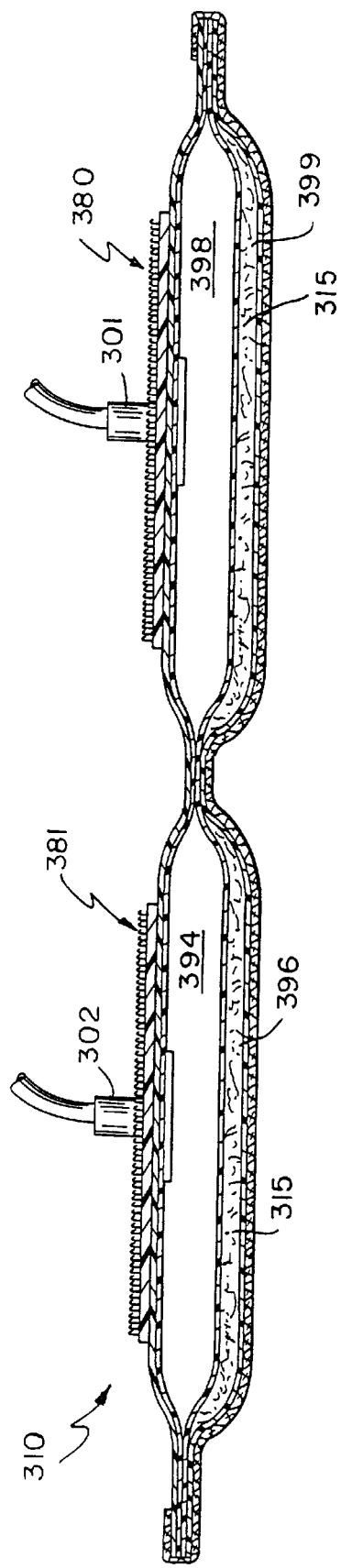
FIG. 7 is a sectional view of the tourniquet of FIG. 6.

In a further embodiment, as shown in FIGS. 6 and 7, a gel-like material 315 is used in a tourniquet cuff 310 of a Bier's Block design, in which the tourniquet has a first air bladder 394 having a first bladder port 302 and a second air bladder 398 having a second bladder port 301, wherein the first and second air bladders 394, 398 are placed in a side-by-side arrangement. Adjacent to first air bladder 394 is placed a first gel cavity 396 with gel-like material 315 disposed therein. Likewise, adjacent to second air bladder 398 is placed a second gel cavity 399 with gel-like material 315 disposed within. It is understood within the scope of this disclosure that the gel-like material in first gel cavity 394 need not be the same as gel-like material in the second gel cavity 396. An inflation device 311, as is known in the art, may be used to inflate air bladders 394 and 398, via first and second bladder ports 302 and 301.

The embodiment illustrated in FIG. 6 is provided with a pair of straps, 390 and 391. As contemplated in this embodiment, each strap would be provided with a fastener, such as VELCRO hook sections, for mating with the VELCRO loop sections 380 and 381. However, it is understood that, rather than straps 390 and 391, the funnel-shaped design best illustrated in FIGS. 1 and 5 could be used with the Bier's Block tourniquet design of FIG. 6.

Figure 8:
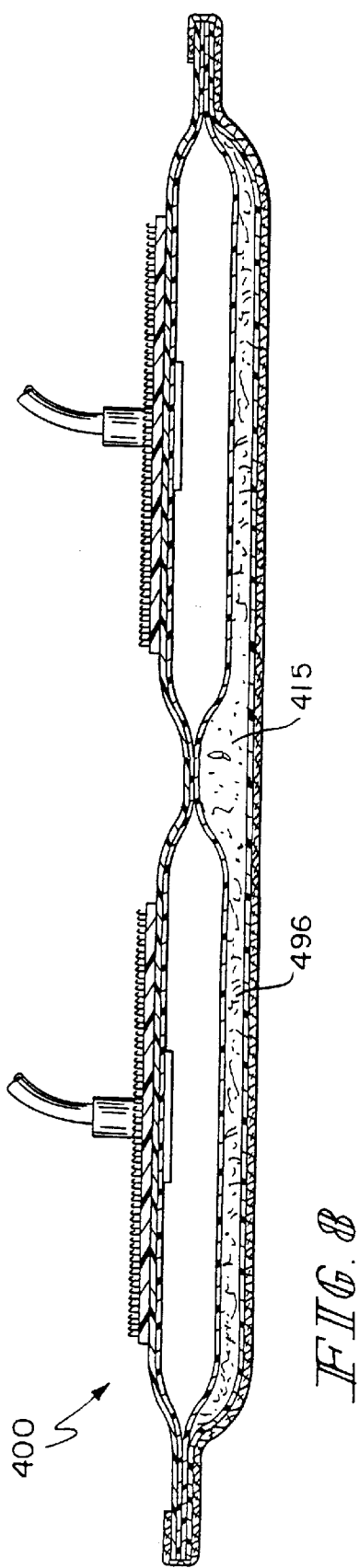
FIG. 8 is a sectional view similar to that shown in FIG. 7 illustrating an additional embodiment of the present invention.

In still another embodiment, a tourniquet 400 (FIG. 8) is provided with first and second gel cavities 396 and 399 (shown in FIG. 7) are replaced by a single gel cavity 496. As with the embodiments described in FIGS. 6 and 7, the gel-like material 415 is placed between air bladders 394 and 398 and the patient's limb.

Referring back to FIGS. 1, 2, 4, and 5, once polyester nap layer 20, middle nylon layer 40, and outer nylon layer 60 have been heat-sealed together, first nap fold portion 27, second nap fold portion 28, and third nap fold portion 29 are folded over first outer nylon side 62 along first, second, and third nap folds 30, 31, and 32, respectively. Once nap fold portions 27, 28, 29 are folded over first outer nylon side 62, it is preferred that nap fold portions 27, 28, 29 are sewn through heat seal 85 with a stitching 86. Other methods of affixing nap fold portions 27, 28, 29 may be used.

As best seen in FIGS. 1 and 5, a first end 91 of VELCRO loop-portion 90 is secured between outer nylon funnel-shaped end 61 of outer nylon layer 60 and polyester nap funnel-shaped end 21 of polyester nap layer 20. Illustratively, stitching 86 continues from nap fold portions 27, 28, 29, as well as along the funnel perimeter 76 of outer nylon funnel-shaped end 61 and polyester nap funnel-shaped end 21, thereby coupling outer nylon funnel-shaped end 61, polyester nap funnel-shaped end 21 and end 91 of VELCRO loop-portion 90. Alternatively, VELCRO loop portion 90 may be an extension of polyester nap funnel-shaped end 21 or outer nylon funnel-shaped end 61. Fixed to main outer nylon body 65 on first outer nylon side 62 is a length of VELCRO hook-portion 80. Tie 120 is fixed to first and second nap fold portions 27 and 28 adjacent and parallel to third nap fold portion 29. Lastly, PVC tube 110 includes a first PVC end 111 fixed to bladder nozzle 102 and a second PVC end 112 fixed to a connector 113. Preferably, connector 113 is an easy-lock connector, as is known in the art. However, other connectors are within the scope of this invention. An inflation device 11 provides a means for inflating air chamber 94 with air or another pressurized fluid.

During use, tourniquet cuff 10 is wrapped around a patient's limb, with polyester nap layer 20 adjacent the patient's limb, so that VELCRO loop-portion 90 engages VELCRO hook-portion 80 securing tourniquet cuff 10 to the patient's limb. Optionally, tie ends 121, 122 of tie 120 are then tied together so that tie 120 is secured around VELCRO loop-portion 90. Air chamber 94 is then be inflated by pumping air through PVC tube 110, through passageway 93 in bladder port 100, and into air chamber 94. With tourniquet cuff 10 wrapped around the patient's limb, gel chamber 96 is positioned between air chamber 94 and the patient's limb. Therefore, when air is pumped into air chamber 94, pressure is exerted around gel chamber 96 which, in turn, transmits pressure around the patient's limb. While VELCRO is utilized in the preferred embodiment, other fasteners, including straps, buckles, snaps, and tape, may be used to secure the tourniquet around a patent's limb.

The gel-like material may be any suitable material that will uniformly distribute the pressure on the patient's limb. Such materials include FLOAM, manufactured by TekSource, Inc. in Draper, UT, FLO-LITE, manufactured by Alden Laboratories, Inc. in Boulder, Colo., and ISOGEL, manufactured by Pittsburgh Plastics, Inc. in Zelienople, Pa. It is understood, however, that the use of other materials would be obvious to one with ordinary skill in the art.

Although the invention has been described in detail with reference to preferred embodiments, variations and modifications exist within the scope and spirit of the invention as described and defined in the following claims.

What is claimed is:

1. A tourniquet cuff comprising:

a first layer having an inner and an outer side, the first layer being impermeable to air;

a second layer having a first and a second side and being impermeable to air, the first layer and the second layer being coupled together to define a first cavity between the inner side of the first layer and the first side of the second layer;

a gel-like material disposed within the first cavity to distribute pressure uniformly on a patient's limb;

a third layer having an inner and an outer side and being impermeable to air, the second layer and the third layer being coupled together to define a second cavity between the second side of the second layer and the inner side of the third layer, the second cavity being inflatable; and a fastener for adjustably securing the tourniquet about the patient's limb with the outer side of the first layer in contact with the patient's limb.

2. The tourniquet cuff of claim 1, wherein the first layer is a polyester nap material and the inner side of the first layer is coated with polyurethane.

3. The tourniquet cuff of claim 1, wherein the first layer is a soft cotton material and the inner side of the first layer is coated with polyurethane.

4. The tourniquet cuff of claim 1, wherein the second layer is a nylon material with a stiffness greater than a 200 denier nylon material.

5. The tourniquet cuff of claim 4, wherein the second layer is about a 420 denier.

6. The tourniquet cuff of claim 5, wherein the second layer is coated with polyurethane.

7. The tourniquet cuff of claim 1, wherein the inner side of the third layer is coated with polyurethane.

8. The tourniquet cuff of claim 1, wherein the third layer has an aperture through which a pressurizing fluid may be introduced.

9. The tourniquet cuff of claim 1, wherein the first, second, and third layers are elongated and at least one of the layers terminates in a tapered end.

10. The tourniquet cuff of claim 9, wherein the fastener is a hook-and-loop fastener closure comprising a first hook-and-loop fastener portion adjacent the tapered end and a second hook-and-loop fastener portion coupled to the outer side of the third layer.

11. The tourniquet cuff of claim 10, wherein the first hook-and-loop fastener portion comprises a loop-portion, and the second hook-and-loop fastener portion comprises a hook-portion.

12. A tourniquet cuff comprising:

means for distributing pressure uniformly around a patient's limb, the means for distributing pressure having an inner portion and an opposite outer portion, the inner portion further having an impervious layer;

means for tightening the pressure distributing means about the patient's limb; the tightening means being positioned to lie adjacent the outer portion; and means for adjustably securing the tourniquet about the patient's limb.

13. The tourniquet cuff of claim 12, wherein the means for tightening is a strap.

14. The tourniquet cuff of claim 12, wherein the means for tightening is an elongated, inflatable cavity.

15. The tourniquet cuff of claim 14, wherein the elongated, inflatable cavity comprises a first end, a second end opposite the first end, a top side extending from the first end to the second end, and a bottom side opposite the top side, the bottom side attached to the elongated gel-filled cavity, and the means for adjustably securing the tourniquet comprises a tapered portion having a wide end and a narrow end, the wide end being coupled to the first end of the elongated, inflatable cavity, a hook-and-loop fastener loop-portion coupled to the narrow end of the tapered portion, and a hook-and-loop fastener hook-portion coupled to the top side of the elongated inflatable cavity.

\* \* \* \* \*